United States Patent [19]
Kumar et al.

[11] Patent Number: 4,980,391

[45] Date of Patent: Dec. 25, 1990

[54] DENTURE ADHESIVES AND METHODS FOR PREPARING SAME

[75] Inventors: Lori D. Kumar, Princeton; Alexander M. Schobel, White House Station, both of N.J.

[73] Assignee: Warner-Lambert Company, Morris Plains, N.J.

[21] Appl. No.: 263,587

[22] Filed: Oct. 27, 1988

[51] Int. Cl.$^5$ .............................. A61K 5/06; C08L 1/14
[52] U.S. Cl. ...................................... 524/45; 524/492; 523/120; 106/35
[58] Field of Search ................... 524/45, 492; 523/120; 106/35, 55

[56] References Cited

U.S. PATENT DOCUMENTS 4,514,528  4/1985  Dhabhar et al. ........................ 524/45
4,521,551  6/1985  Chang et al. ........................... 523/120

*Primary Examiner*—Nathan M. Nutter
*Attorney, Agent, or Firm*—Carl W. Battle; Charles A. Gaglia, Jr.

[57] ABSTRACT

The present invention pertains to denture adhesive compositions comprising a substantially anhydrous mixture, in percentages by weight, of an adhesive component comprised of a mixture of (a) from about 29 to about 34% of a mixed, partial calcium/sodium salt of a methyl vinyl ether-maleic anhydride-type copolymer, and (b) from about 22 to about 26% sodium carboxymethylcellulose; a vehicle component comprises of a mixture of (c) from about 20 to about 26% petrolatum and from about 15 to about 24% mineral oil; and a hydration and tackifier component comprised of (d) from about 0.5 to about 2% silicon dioxide and (e) from about 1 to about 3% poly(ethylene oxide) homopolymer. The present invention also pertains to methods by which these denture adhesive compositions may be prepared.

19 Claims, No Drawings

DENTURE ADHESIVES AND METHODS FOR PREPARING SAME

BACKGROUND OF THE INVENTION

1. Field of the Invention

This invention pertains to improved denture adhesive compositions which provide superior adhesion properties. More particularly, this invention pertains to denture adhesive compositions which comprise an adhesive component comprising a mixture of a mixed, partial calcium/sodium salt of a methyl vinyl ether-maleic anhydride-type copolymer and sodium carboxymethylcellulose, a vehicle component comprising a mixture of petrolatum and mineral oil, and a hydration and tackifier component comprising silicon dioxide and poly(ethylene oxide) homopolymer. This invention also pertains to methods by which these improved denture adhesive compositions may be prepared.

2. Description of the Prior Art

Denture adhesive compositions are generally prepared from natural or synthetic polymeric materials suspended in an oleaginous vehicle system. Upon contact with water, these polymeric materials have the property of swelling to several times their original volume to form a gelatinous mass which can fill the space, act as a cushion and provide adhesion between a denture plate and gum tissue.

Some commonly noted deficiencies with denture adhesive compositions are phase separation of the adhesive composition, the need for more than one application of the adhesive composition per day and oozing of the adhesive composition from under the denture plate. Phase separation of the adhesive composition causes loss of the oily vehicle component which results in an excessively thick denture adhesive composition. Multiple applications of the adhesive composition are generally undesirable. Oozing of the denture adhesive composition from under the denture plate, usually the result of excessive swelling of the adhesive composition during hydration, is a major drawback because of the resulting unplesant taste, unpleasant mouth feel and loss of adhesive composition from under the denture plate. Insufficient swelling of the denture adhesive composition, on the other hand, results in an adhesive composition which provides insufficient space filling and cushioning properties under the denture plate.

U.S. Pat. No. 2,978,812, issued to Rosenthal et al. and assigned to Block Drug Company, Inc., discloses the use of poly(ethylene oxide) homopolymer as a denture adhesive. When wetted, the poly(ethylene oxide) homopolymer is said to form a gel which has a high degree of tackiness.

U.S. Pat. No. 3,003,988, issued to Germann et al. and assigned to Clark-Cleveland Incorporated, discloses the use of mixed, partial salts of lower alkyl vinyl of ether-maleic anhydride-type copolymers as water-sensitized, water-insoluble denture stabilizers.

U.S. Pat. No. 3,380,876, issued to Rusher and assigned to E. I. duPont de Nemours and Company, discloses the use of colloidal silicon dioxide particles containing a minor amount of an organic additive to bond thermoplastic materials to a substrate. The organic additive is selected from the group consisting of polyethylene glycol, tert-dodecylthioether, polyoxyethylene sorbitan monolaurate and water-soluble resins of poly(ethylene oxide) homopolymer.

U.S. Pat. No. 3,736,274, issued to Schoenholz et al. and assigned to Foremost-McKesson, Inc., discloses a denture adhesive composition comprised of (a) a polymeric material selected from the group consisting of lower alkyl vinyl ether-maleic anhydride and/or acid-type copolymers, (b) a polymeric N-vinyl lactam, and (c) sodium carboxymethylcellulose.

U.S. Pat. No. 4,514,528, issued to Dhabhar et al. and assigned to Richardson-Vicks Inc., discloses a hydrophilic denture adhesive composition comprising an adhesive polymeric fraction consisting essentially of mixed, partial salts of lower alkyl vinyl ether-maleic anhydride-type copolymers with sodium carboxymethylcellulose and/or poly(ethylene oxide) homopolymer and a vehicle fraction comprising polyethylene glycol.

U.S. Pat. No. 4,518,721, issued to Dhabhar et al. and assigned to Richardson-Vicks Inc., discloses a hydrophilic denture adhesive composition consisting essentially of sodium carboxymethylcellulose and poly(ethylene oxide) homopolymer in a hydrophilic vehicle comprising polyethylene glycol.

U.S. Pat. No. 4,522,956, issued to Dhabhar et al. and assigned to Richardson-Vicks Inc., discloses a hydrophilic denture adhesive composition consisting essentially of poly(ethylene oxide) homopolymer as the adhesive component and polyethylene glycol as the vehicle component.

U.S. Pat. No. 4,530,942, issued to Dhabhar et al. and assigned to Richardson-Vicks Inc., discloses a hydrophilic denture adhesive composition consisting essentially of sodium carboxymethylcellulose as the adhesive component and polyethylene glycol as the hydrophilic vehicle component.

U.S. Pat. No. 4,569,955, issued to Dhabhar and assigned to Richardson-Vicks Inc., discloses a denture adhesive composition consisting essentially of an adhesive polymeric fraction consisting essentially of a mixed, partial salt of a lower alkyl vinyl ether-maleic anhydride-type copolymer and sodium carboxymethylcellulose in a vehicle component consisting essentially of mineral oil thickened with polyethylene.

European patent application EPO No. 265 916 A2, assigned to Richardson-Vicks Inc., discloses a denture stabilizing composition which contains unmixed, partial zinc and strontium salts of lower alkyl vinyl ether-maleic acid type copolymers.

While all of the above denture adhesive compositions provide some degree of denture stability, none of the above products can accommodate the many variations in temperature, pH and mechanical agitation which are normal in the oral cavity over a prolonged period of time. Hence, there is still a need for denture adhesive compositions which have superior adhesive properties over prolonged periods of time. The present invention provides such improved denture adhesive compositions with superior adhesive properties over prolonged periods of time and under varied conditions without the organoleptic disadvantages characteristic of previously known products. The present invention also provides methods by which these improved denture adhesive compositions may be prepared.

SUMMARY OF THE INVENTION

The present invention pertains to denture adhesive compositions comprising a substantially anhydrous mixture, in percentages by weight, of an adhesive component comprised of a mixture of (a) from about 29 to about 34% of a mixed, partial calcium/sodium salt of a methyl vinyl ether-maleic anhydride-type copolymer, and (b) from about 22 to about 26% sodium carboxymethylcellulose; a vehicle component comprised of a mixture of (c) from about 20 to about 26% petrolatum and from about 15 to about 24% mineral oil; and a hydration and tackifier component comprised of (d) from about 0.5 to about 2% silicon dioxide and (e) from about 1 to about 3% poly(ethylene oxide) homopolymer. The present invention also pertains to methods by which these denture adhesive compositions may be prepared.

DETAILED DESCRIPTION OF THE INVENTION

The present invention pertains to improved denture adhesive compositions which provide superior adhesive properties over a prolonged period of time. More particularly, this invention relates to denture adhesive compositions comprising a substantially anhydrous mixture of an adhesive component comprised of a mixture of (a) a mixed, partial calcium/sodium salt of a methyl vinyl ether-maleic anhydride-type copolymer, and (b) sodium carboxymethylcellulose; a vehicle component comprised of (c) a mixture of petrolatum and mineral oil; and a hydration and tackifier component comprised of (d) silicon dioxide and (e) poly(ethylene oxide) homopolymer. This invention also relates to methods by which these improved denture adhesive compositions may be prepared.

The amounts of the ingredients in each component in the present denture adhesive compositions may be varied within certain ranges to provide denture adhesive products suitable for use in this invention. In a preferred embodiment, the improved denture adhesive compositions of the present invention comprise a substantially anhydrous mixture, in percentages by weight, of (a) from about 29 to about 34% of a mixed, partial calcium/sodium salt of a methyl vinyl ether-maleic anhydride-type copolymer, (b) from about 22 to about 26% sodium carboxymethylcellulose, (c) from about 20 to about 26% petrolatum and from about 15 to about 24% mineral oil, (d) from about 0.5 to about 2% silicon dioxide, and (e) from about 1 to about 3% poly(ethylene oxide) homopolymer. In a more preferred embodiment, the improved denture adhesive compositions of the present invention comprise a substantially anhydrous mixture, in percentages by weight, of (a) from about 29 to about 33% of a mixed, partial calcium/sodium salt of a methyl vinyl ether-maleic anhydride-type copolymer, (b) from about 23 to about 26% sodium carboxymethylcellulose, (c) from about 22 to about 26% petrolatum and from about 16 to about 22% mineral oil, (d) from about 0.75 to about 1.75% silicon dioxide, and (e) from about 1 to about 2.75% poly(ethylene oxide) homopolymer. In a most preferred embodiment, the improved denture adhesive compositions of the present invention comprise a substantially anhydrous mixture, in percentages by weight, of (a) from about 29 to about 30% of a mixed, partial calcium/sodium salt of a methyl vinyl ether-maleic anhydride-type copolymer, (b) from about 25 to about 26% sodium carboxymethylcellulose, (c) from about 25 to about 26% petrolatum and from about 16 to about 20% mineral oil, (d) from about 1 to about 1.5% silicon dioxide, and (e) from about 1.5 to about 2% poly(ethylene oxide) homopolymer.

The ratio of the amount of the ingredients in the adhesive component, the mixed, partial calcium/sodium salt of a methyl vinyl ether-maleic anhydride-type copolymer and sodium carboxymethylcellulose, may be varied within certain ranges to provide denture adhesive products suitable for use. Preferably, the mixed, partial calcium/sodium salt of a methyl vinyl ether-maleic anhydride-type copolymer and sodium carboxymethylcellulose are present in a weight ratio of from about 2.75:1 to about 1:1, respectively, more preferably, in a weight ratio of from about 2:1 to about 1:1, respectively, and most preferably, in a weight ratio of from about 1.2:1 to about 1:1, respectively.

The ratio of the amount of the ingredients in the vehicle component, petrolatum and mineral oil, may be varied within certain ranges to provide denture adhesive products suitable for use. Preferably, petrolatum and mineral oil are present in a weight ratio of from about 1.7:1 to about 1:1, respectively, more preferably, in a weight ratio of from about 1.5:1 to about 1:1, respectively, and most preferably, in a weight ratio of from about 1.2:1 to about 1:1, respectively.

The improved denture adhesive compositions of the present invention include an adhesive component comprised of a mixture of a mixed, partial calcium/sodium salt of a methyl vinyl ether-maleic anhydride-type copolymer and sodium carboxymethylcellulose. In addition to providing adhesive properties, these adhesive component ingredients also provide cushioning under the denture plate.

Mixed, partial calcium/sodium salts of methyl vinyl ether-maleic anhydride-type copolymers (Ca/Na salts of MVE/MA, Ca/Na-MVE/MA) and the polymerization techniques used to obtain these copolymers are well known in the art. The mole ratio of the methyl vinyl ether monomer component to the maleic anhydride monomer component is substantially unity.

The mixed, partial calcium/sodium salts of the methyl vinyl ether-maleic anhydride-type copolymers employed in the present invention contain about 20–36% of the initial carboxyl groups of the polymer unreacted, have a calcium to sodium mole ratio of from about 2.5:1 to about 4:1, and have a calcium content in the range of from about 9.6 to about 13%, per initial carboxyl group. The apparent minimum bulk density of the polymer is about 0.5 g/cc and the pH of a 1% aqueous solution of the powder by weight is about 6–7. The particle size of the mixed, partial calcium/sodium salts of methyl vinyl ether-maleic anhydride-type copolymers employed should be such that at least about 95.5% of the particles pass through a 200 mesh screen and only about 0.5% of the particles are retained on a 140 mesh screen.

In a preferred embodiment, the mixed, partial calcium/sodium salt of the methyl vinyl ether-maleic anhydride-type copolymer has a calcium content of about 12%, by weight, and a particle size of about 30–45 microns. A suitable preferred mixed, calcium/sodium partial salt of a methyl vinyl ether-maleic anhydride-type copolymer is Gantrez MS955, a commercially available product manufactured by GAF Corporation, Wayne, N.J.

Sodium carboxymethylcellulose (Na-CMC) is a white to off-white powder which when hydrated develops a tacky or gummy consistency with adhesive characteristics. The sodium carboxymethylcellulose gums employed in the present invention are water soluble, anionic, long chain polymers derived from cellulose. Properties of the gums vary with the average number of carboxymethyl groups substituted per anhydroglucose unit in each cellulose molecule. This carboxygroup substitution characteristic is generally referred to as the "degree of substitution," with the maximum degree of substitution possible designated as "3.0," since there are a maximum of three reactive hydroxyl groups in each anhydroglucose unit.

Sodium carboxymethylcellulose gums of the type employed in the present invention are more fully described in "Chemical and Physical Properties: Cellulose Gum," 1978, published by Hercules, Incorporated, Wilmington, Del.

In a preferred embodiment, the cellulose gums of the present invention have a degree of substitution of from about 0.4 to about 1.2. The viscosity of a 1% aqueous solution of such gums, measured at 25° C., should be in the range of from about 400 to about 4,500, and preferably from about 1,500 to about 3,000 centipoises. The particle size of the preferred cellulose gums employed in the present invention should be such that the cellulose particles will not produce a gritty mouth feel, and only about 0.5% of the particles will be retained on a 60 mesh screen. A suitable preferred sodium carboxymethylcellulose gum is CMC 7HXF, a commercially available product manufactured by Aqualon Company, Wilmington, Del.

The improved denture adhesive compositions of the present invention also include a vehicle component comprised of a mixture of petrolatum and mineral oil.

Petrolatum is a colorless to amber, oily, translucent, purified mixture of semi-solid hydrocarbons obtained from petroleum. Preferred petrolatum waxes employed in the present invention have a congealing point at about 59°–60° C. and a viscosity of from about 8.16 to about 14.24 centistokes at 98° C. In a preferred embodiment, the petrolatum is Penreco Blend B5 Special, a commercially available product manufactured by Penreco, a division of Pennzoil Products Company, Karns, Pa.

Mineral oil is a colorless, transparent, oily mixture of liquid hydrocarbons obtained from petroleum. Preferred mineral oils employed in the present invention are highly refined white oils having a maximum viscosity of about 33.5 centistokes at 40° C., a specific gravity of about 0.818 to about 0.880 at 25° C. and which meet United States Pharmacopeia specifications as to taste, odor and acid. In a preferred embodiment, the mineral oil is Light Mineral Oil-USP, Mineral Oil CTFA, a commercially available product manufactured by Witco Chemical Company, Perth Amboy, N.J.

The improved denture adhesive compositions of the present invention also include a hydration and tackifier component comprised of silicon dioxide and poly(ethylene oxide) homopolymer. In addition to aiding hydration, silicon dioxide also acts as an oil absorber thereby controlling syneresis. Poly(ethylene oxide) homopolymer also provides tack and adhesiveness, absorbs oil, and improves mouth feel while enhancing the functionality of the final product.

Silicon dioxide is a transparent, tasteless, crystalline or amorphous powdery material which is practically insoluble in water. Preferably the silicon dioxide employed in the present invention is fumed silicon dioxide which is a colloidal, synthetic, amorphous form of silicon dioxide made by combustion of silicon tetrachloride in hydrogen-oxygen furnaces.

In a preferred embodiment, the fumed silicon dioxide has a surface area of about 380 $m^2/g$, a standard bulk density of about 0.007 $lbs/ft^3$, and a specific gravity of about 2.2. The pH of a 4% aqueous slurry of the fumed silicon dioxide is about 3.6–4.3. A suitable preferred fumed silicon dioxide is CAB-O-SIL EH5, a commercially available silicon dioxide product manufactured by Cabot Corporation, CAB-O-SIL Division, Tuscola, Ill.

Poly(ethylene oxide) polymers (PEO) are water soluble, non-ionic, polyether homopolymers having molecular weights from about 100,000 to about 5,000,000. The homopolymers are white powders which when hydrated develop into a gelatinous mass having adhesive characteristics. The polyether polymers have the chemical structure —$(CH_2CH_2O)_n$- wherein n represents the degree of polymerization of the polymer and may have a value from about 2,000 to about 100,000.

Poly(ethylene oxide) homopolymers of the type employed in the present invention are more fully described in "Polyox," 1978, published by Union Carbide Corporation, New York, N.Y., as Technical Bulletin F-44029B.

In a preferred embodiment, the poly(ethylene oxide) homopolymer employed in the present invention has a molecular weight of about 400,000, a melting point of about 65° C., a bulk density of about 384 $kg/m^3$ and a viscosity of from about 2.25 to about 4.50 centipoises (5% aqueous solution at 25° C.). Preferably, the particle size of the homopolymer should be such that 100% of the particles pass through a 60 mesh standard sieve. A suitable preferred poly(ethylene oxide) homopolymer is Polyox WSR N-3000, a commercially available product manufactured by Union Carbide Corporation, Specialty Chemicals Division, Danbury, Conn.

Any suitable conventional additive generally employed in denture adhesive compositions may be used in the present invention. Such additives include flavoring agents, coloring agents, preservatives, odorants, deodorants, natural and synthetic sweeteners, antimicrobial agents, tissue healing agents and the like. Preferably, such additives, when present, are used in amounts up to about 1%, by weight of the total composition.

The combination of the adhesive components, the vehicle components and the hydration and tackifier components, as set out above, in the proportions disclosed, results in improved denture adhesive compositions having superior adhesive properties over prolonged periods of time and under varied conditions. The superior adherent properties are markedly greater than that expected by mere combination of the denture adhesive components. The instant denture adhesive compositions, when applied to denture plates and exposed to moisture, hydrates to form adhesive compositions with markedly superior denture stabilizing properties without objectionable phase separation or oozing of the composition from under a denture plate.

The present invention extends to methods of making the improved denture adhesive compositions. The final denture adhesive compositions are readily prepared using methods generally known in the denture adhesive technology. In such a method, a denture adhesive composition is made by preparing a mixture by admixing the ingredients in the adhesive component and the ingredients in the hydration and tackifier component into the ingredients in the vehicle component in a mixing vessel. Optional additives such as coloring agents, preservatives and flavoring agents may also be admixed. Additional optional ingredients may be incorporated into the denture adhesive composition as dictated by the nature of the desired final product as well as by those having ordinary skill in the art. The finished product is then discharged from the mixing vessel and stored in an appropriate container for later packaging.

The apparatus useful in accordance with the present invention comprises mixing, heating and evacuation apparatus well known in the denture adhesive manufacturing arts, and therefore the selection of the specific apparatus will be apparent to the artisan.

The present invention is further illustrated by the following examples which are not intended to limit the effective scope of the claims. All parts and percentages in the examples and throughout the specification and claims are by weight of the final composition unless otherwise specified.

EXAMPLE 1

Inventive Run 1

This example demonstrates a method for preparing an improved denture adhesive product according to the process of the present invention having the composition set out in Table 1.

TABLE 1

| INGREDIENT | PERCENT BY WEIGHT |
| --- | --- |
| Ca/Na salt of MVA/MA | 29.63 |
| Na—CMC | 24.69 |
| petrolatum | 20.98 |
| mineral Oil | 20.98 |
| fumed silicon dioxide | 1.48 |
| PEO | 1.98 |
| flavoring agent | 0.08 |
| coloring agent | 0.03 |
| methyl paraben | 0.05 |
| propyl paraben | 0.10 |

(a) A first mixture was prepared by admixing the mixed, partial calcium/sodium salt of the methyl vinyl ether-maleic anhydride-type copolymer (Ca/Na salt of MVA/MA) and the sodium carboxymethylcellulose (Na-CMC) with the fumed silicon dioxide and the poly(ethylene oxide) homopolymer (PEO) in a mixing vessel. The coloring agent was also admixed into the first mixture.

(b) A second mixture was prepared by admixing the petrolatum and mineral oil in a low shear mixer (75 kilogram capacity), heating the ingredients to about 33° C. while mixing the ingredients at about 12 rpm. The preservatives, methyl paraben and propyl paraben, and the flavoring agent were then admixed into the second mixture with stirring continued for about 5 minutes.

(c) The first mixture from step (a) was admixed into the second mixture from step (b) with the mixing speed held at about 12 rpm over a period of about twenty minutes. The mixing vessel containing the resulting mixture was then sealed and the pressure in the vessel was dropped to about 500-650 mm Hg. The mixture was stirred for a period of about one hour at a mixing speed of about 28 rpm. The finished denture adhesive product was discharged from the mixing vessel and stored in an appropriate container for later packaging.

An organoleptic evaluation test was performed on the denture adhesive product in Table 1 by several expert evaluation panels of approximately 25 persons each. The denture adhesive product of Table 1 was judged to provide superior denture stabilizing properties and did not exhibit objectionable phase separation or oozing of the composition from a dental plate.

EXAMPLE 2

Inventive Run 2

This example demonstrates a method for preparing an improved denture adhesive product according to the process of the present invention having the composition set out in Table 2.

TABLE 2

| INGREDIENT | PERCENT BY WEIGHT |
| --- | --- |
| Ca/Na salt of MVA/MA | 29.63 |
| Na—CMC | 24.69 |
| petrolatum | 21.98 |
| mineral oil | 19.98 |
| fumed silicon dioxide | 1.48 |
| PEO | 1.98 |
| flavoring agent | 0.07 |
| coloring agent | 0.04 |
| methyl paraben | 0.05 |
| propyl paraben | 0.10 |

The denture adhesive composition in Table 2 was prepared according to the procedure described in example 1.

An organoleptic evaluation test was performed on the denture adhesive product in Table 2 by several expert evaluation panels of approximately 25 persons each. The denture adhesive product of Table 2 was judged to provide superior denture stabilizing properties and did not exhibit objectionable phase separation or oozing of the composition from a dental plate.

EXAMPLE 3

Inventive Run 3

This example demonstrates a method for preparing an improved denture adhesive product according to the process of the present invention having the composition set out in Table 3.

TABLE 3

| INGREDIENT | PERCENT BY WEIGHT |
| --- | --- |
| Ca/Na salt of MVA/MA | 29.63 |
| Na—CMC | 24.69 |
| petrolatum | 25.50 |
| mineral oil | 16.47 |
| fumed silicon dioxide | 1.48 |
| PEO | 1.98 |
| flavoring agent | 0.06 |
| coloring agent | 0.04 |
| propyl paraben | 0.10 |

The denture adhesive composition in Table 3 was prepared according to the procedure described in example 1.

An organoleptic evaluation test was performed on the denture adhesive product in Table 3 by several expert evaluation panels of approximately 25 persons each. The denture adhesive product of Table 3 was judged to provide superior denture stabilizing properties and did not exhibit objectionable phase separation or oozing of the composition from a dental plate.

EXAMPLES 4-11

Comparative Runs 1, 4-11

These examples demonstrate comparative denture adhesive products having the compositions set out in Table 4 and prepared by the procedure described in example 1. The composition of the denture adhesive product described in example 1 is also set out in Table 4 for comparative purposes.

TABLE 4

| Ingredient (Percent by Weight) | EXAMPLES | | | | | | | | |
|---|---|---|---|---|---|---|---|---|---|
| | 1 | 4 | 5 | 6 | 7 | 8 | 9 | 10 | 11 |
| Ca/Na-MVA/MA | 29.63 | 24.63 | 26.03 | 37.50 | 40.00 | 33.14 | 30.00 | 30.00 | 32.63 |
| Na/CMC | 24.69 | 24.69 | 25.71 | 16.83 | 13.00 | 23.56 | 25.00 | 25.00 | 24.68 |
| petrolatum | 20.98 | 23.48 | 22.20 | 21.01 | 24.81 | 20.10 | 21.12 | 20.62 | 20.76 |
| mineral oil | 20.98 | 23.48 | 22.20 | 21.01 | 15.03 | 20.11 | 21.12 | 20.62 | 20.27 |
| fumed silicon dioxide | 1.48 | 1.48 | 1.59 | 1.50 | — | 0.96 | 1.50** | 1.50 | 0.50 |
| PEO | 1.98 | 1.98* | 2.09* | 1.97* | 1.98 | 1.89 | 1.00 | 2.00*** | 1.89 |
| flavor | 0.08 | 0.10 | — | — | — | 0.07 | 0.10 | 0.10 | 0.07 |
| color | 0.03 | 0.01 | 0.03 | 0.03 | 0.03 | 0.03 | 0.01 | 0.01 | 0.03 |
| methyl paraben | 0.05 | 0.05 | 0.05 | 0.05 | 0.05 | 0.05 | 0.05 | 0.05 | 0.05 |
| propyl paraben | 0.10 | 0.10 | 0.10 | 0.10 | 0.10 | 0.09 | 0.10 | 0.10 | 0.10 |
| carrageenan | — | — | — | — | 5.00 | — | — | — | — |

*Polyox WSR N-301
**CAB-O-SIL M-5
***Polyox WSR N-12K

The fumed silicon dioxide used in the denture adhesive compositions in Table 4 was CAB-O-SIL EH5 except in the denture adhesive composition of example 9 where CAB-O-SIL M-5 was used instead. The poly(ethylene oxide) homopolymer (PEO) used in the denture adhesive compositions of Table 4 was Polyox WSR N-3000 except in the denture adhesive compositions of examples 4, 5 and 6 where Polyox WSR N-301 was used instead and in the denture adhesive composition of example 10 where Polyox WSR N-12K was used instead.

An organoleptic evaluation test was performed on the denture adhesive products in Table 4 by several expert evaluation panels of approximately 25 persons each. The denture adhesive products of examples 4–11 were each compared against the denture adhesive products of example 1.

The denture adhesive product of example 4 contained less Ca/Na-MVA/MA than the product of example 1, more petrolatum and mineral oil than the product of example 1 and Polyox WSR N-301 instead of Polyox WSR N-3000. The denture adhesive product of example 4 was judged to have decreased adhesiveness, increased oiling out properties and an unpleasant aftertaste and slippery mouth feel.

The denture adhesive product of example 5 contained less Ca/Na-MVA/MA and more petrolatum and more mineral oil than the product of example 1 and Polyox WSR N-301 instead of Polyox WSR N-3000. The denture adhesive product of example 5 was also judged to have decreased adhesiveness, increased oiling out properties and an unpleasant aftertaste and slippery mouth feel.

The denture adhesive product of example 6 contained more Ca/Na-MVA/MA and less sodium carboxymethylcellulose (Na-CMC) than the product in example 1 and Polyox WSR N-301 instead of Polyox WSR N-3000. The denture adhesive product of example 6 was judged to have a decrease in hydration properties and a concomitant decrease in cushioning, adhesiveness and overall comfort.

The denture adhesive product of example 7 contained carrageenan, more Ca/Na-MVA/MA, less sodium carboxymethylcellulose, no fumed silicon dioxide, and a different ratio of petrolatum to mineral oil than the product in example 1. The denture adhesive product of example 7 was judged to have a decrease in hydration properties and a concomitant decrease in adhesiveness and also an increase in stiffness.

The denture adhesive product of example 8 contained more Ca/Na-MVA/MA, slightly less sodium carboxymethylcellulose and less fumed silicon dioxide than the product of example 1. The denture adhesive product of example 8 was judged to have comparable hydration and adhesiveness with that of the denture adhesive composition of example 1 but was also judged to have increased oiling out properties.

The denture adhesive product of example 9 contained CAB-O-SIL M-5 instead of CAB-O-SIL EH5. The denture adhesive product of example 9 was judged to have excessively fast hydration properties with a resulting loss in adhesiveness.

The denture adhesive product of example 10 contained Polyox WSR N-12K instead of Polyox WSR N-3000. The denture adhesive product of example 10 was judged to have excessively fast hydration properties with a resulting loss in adhesiveness and an increase in oozing out properties.

The denture adhesive product of example 11 contained less fumed silicon dioxide than the product in example 1. The denture adhesive product of example 11 was judged to have a decrease in hydration properties and a concomitant decrease in adhesiveness with a resulting loss in long term stability of the product.

The invention being thus described, it will be obvious that the same may be varied in many ways. Such variations are not to be regarded as a departure from the spirit and scope of the invention and all such modifications are intended to be included within the scope of the following claims.

We claim:

1. A denture adhesive composition comprising a substantially anhydrous mixture, in percentages by weight, of:
   (a) from about 29 to about 34% of a mixed, partial calcium/sodium salt of a methyl vinyl ether-maleic anhydride-type compolymer, wherein said salt has a calcium content in the range of from about 9.6 to about 13% by weight and a calcium to sodium mole ratio of from about 2.5:1 to about 4:1;
   (b) from about 22 to about 26% sodium carboxymethylcellulose;
   (c) from about 20 to about 26% petrolatum and from about 15 to about 24% mineral oil;
   (d) from about 0.5 to about 2% silicon dioxide; and
   (e) from about 1 to about 3% poly(ethylene oxide) homopolymer.

2. The denture adhesive composition according to claim 1 wherein the mixed, partial calcium/sodium salt of a methyl vinyl ether-maleic anhydride-type copolymer is present in an amount from about 29 to about 33% and sodium carboxymethylcellulose is present in an amount from about 23 to about 26%, by weight of the total composition.

3. The denture adhesive composition according to claim 2 wherein the mixed, partial calcium/sodium salt of a methyl vinyl ether-maleic anhydride-type copolymer is present in an amount from about 29 to about 30% and sodium carboxymethylcellulose is present in an amount from about 25 to about 26%, by weight of the total composition.

4. The denture adhesive composition according to claim 1 wherein petrolatum is present in an amount from about 22 to about 26% and mineral oil is present in an amount from about 16 to about 22%, by weight of the total composition.

5. The denture adhesive composition according to claim 4 wherein petrolatum is present in an amount from about 25 to about 26% and mineral oil is present in an amount from about 16 to about 20%, by weight of the total composition.

6. The denture adhesive composition according to claim 1 wherein silicon dioxide is present in an amount from about 0.75 to about 1.75% and poly(ethylene oxide) homopolymer is present in an amount from about 1 to about 2.75%, by weight of the total composition.

7. The denture adhesive composition according to claim 6 wherein silicon dioxide is present in an amount from about 1 to about 1.5% and poly(ethylene oxide) homopolymer is present in an amount from about 1.5 to about 2%, by weight of the total composition.

8. The denture adhesive composition according to claim 1 wherein the mixed, partial calcium/sodium salt of a methyl vinyl ether-maleic anhydride-type copolymer and sodium carboxymethylcellulose are present in a weight ratio of from about 2.75:1 to about 1:1, respectively.

9. The denture adhesive composition according to claim 8 wherein the mixed, partial calcium/sodium salt of a methyl vinyl ether-maleic anhydride-type copolymer and sodium carboxymethylcellulose are present in a weight ratio of from about 2:1 to about 1:1, respectively.

10. The denture adhesive composition according to claim 9 wherein the mixed, partial calcium/sodium salt of a methyl vinyl ether-maleic anhydride-type copolymer and sodium carboxymethylcellulose are present in a weight ratio of from about 1.2:1 to about 1:1, respectively.

11. The denture adhesive composition according to claim 1 wherein petrolatum and mineral oil are present in a weight ratio of from about 1.7:1 to about 1:1, respectively.

12. The denture adhesive composition according to claim 11 wherein petrolatum and mineral oil are present in a weight ratio of from about 1.5:1 to about 1:1, respectively.

13. The denture adhesive composition according to claim 12 wherein petrolatum and mineral oil are present in a weight ratio of from about 1.2:1 to about 1:1, respectively.

14. The denture adhesive composition according to claim 1 wherein the mixed, partial calcium/sodium salt of a methyl vinyl ether-maleic anhydride-type copolymer has a calcium content of about 12%, by weight.

15. The denture adhesive composition according to claim 1 wherein the mixed, partial calcium/sodium salt of a methyl vinyl ether-maleic anhydride-type copolymer has a particle size of about 30–45 microns.

16. A denture adhesive composition of claim 1 comprising a substantially anhydrous mixture, in percentages by weight, of:
   (a) about 29.6% of a mixed, partial calcium/sodium salt of a methyl vinyl ether-maleic anhydride-type copolymer;
   (b) about 24.7% sodium carboxymethylcellulose;
   (c) about 21% petrolatum and about 21% mineral oil;
   (d) about 1.5% silicon dioxide; and
   (e) about 2% poly(ethylene oxide) homopolymer.

17. A denture adhesive composition of claim 1 comprising a substantially anhydrous mixture, in percentages by weight, of:
   (a) about 29.6% of a mixed, partial calcium/sodium salt of a methyl vinyl ether-maleic anhydride-type copolymer;
   (b) about 24.7% sodium carboxymethylcellulose;
   (c) about 22% petrolatum and about 20% mineral oil;
   (d) about 1.5% silicon dioxide; and
   (e) about 2% poly(ethylene oxide) homopolymer.

18. A denture adhesive composition of claim 1 comprising a substantially anhydrous mixture, in percentages by weight, of:
   (a) about 29.6% of a mixed, partial calcium/sodium salt of a methyl vinyl ether-maleic anhydride-type copolymer;
   (b) about 24.7% sodium carboxymethylcellulose;
   (c) about 25.5% petrolatum and about 16.5% mineral oil;
   (d) about 1.5% silicon dioxide; and
   (e) about 2% poly(ethylene oxide) homopolymer.

19. A method for preparing a denture adhesive composition comprising a substantially anhydrous mixture comprising the steps of:
   A. providing the following ingredients, in percentages by weight, of:
      (a) from about 29 to about 34% of a mixed, partial calcium/sodium salt of a methyl vinyl ether-maleic anhydride-type copolymer wherein said salt has a calcium content in the range of about 9.6 to about 13% by weight and a calcium to sodium mole ratio of from about 2.5:1 to about 4:1;
      (b) from about 22 to about 26% sodium carboxymethylcellulose;
      (c) from about 20 to about 26% petrolatum and from about 15 to about 24% mineral oil;
      (d) from about 0.5 to about 2% silicon dioxide; and
      (e) from about 1 to about 3% poly(ethylene oxide) homopolymer;
   B. preparing a mixture by admixing the ingredients in steps (a), (b), (d) and (e) with the ingredients in step (c).

* * * * *